United States Patent [19]
Schwan

[11] 3,974,169
[45] Aug. 10, 1976

[54] α-[2-(2-PYRIDYL)ETHYLAMINO]-PHENYLACETIC ACID DIHYDROCHLORIDE HEMIHYDRATE

[75] Inventor: Thomas J. Schwan, Norwich, N.Y.

[73] Assignee: Morton-Norwich Products, Inc., Norwich, N.Y.

[22] Filed: May 12, 1975

[21] Appl. No.: 576,344

[52] U.S. Cl. .............................. 260/295 R; 424/263
[51] Int. Cl.² ........................................ C07D 213/04
[58] Field of Search ................................ 260/295 R

[56] References Cited
OTHER PUBLICATIONS

Bruzzese et al., J. Pharm. Sci., vol. 55, (1966), pp. 737–740.
Ohta et al., Chemical Abstracts, 54:22634h, (1960).

Primary Examiner—Norman A. Drezin
Attorney, Agent, or Firm—Anthony J. Franze

[57] ABSTRACT

A compound α-[2-(2-Pyridyl)ethylamino]phenylacetic acid dihydrochloride Hemihydrate possesses pharmacological activity as an antihypertensive agent.

1 Claim, No Drawings

α-[2-(2-PYRIDYL)ETHYLAMINO]PHENYLACETIC ACID DIHYDROCHLORIDE HEMIHYDRATE

This invention relates to chemical compounds. In particular it is concerned with a compound of the formula:

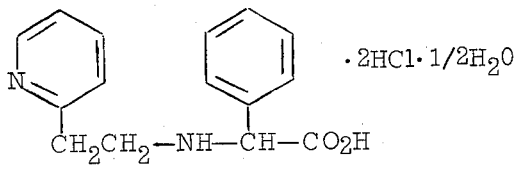 · 2HCl · 1/2H$_2$O

When administered subcutaneously or orally to animals this compound exhibits antihypertensive activity. Administration of 100 mg/kg/day of this compound to rats for 7 days caused marked inhibition of the response to norephinephrine, renin and angiotensin.

In order that this invention be readily available to and understood by those skilled in the art the following illustrative examples are supplied:

EXAMPLE I

Ethyl α-[2-(2-pyridyl)ethylamino]phenylacetate Dihydrochloride Hydrate

A solution of ethyl α-bromophenylacetate (85 g., 0.35 mole) and 100 ml. of ethyl ether was added to a slution of 2-(2-aminoethyl)pyridine, (42.7 g., 0.35 mole), triethylamine (35.3 g., 0.35 mole) and 250 ml. of ethyl ether. The suspension was refluxed for 3.5 hours and cooled. The inorganic salts were filtered and the solvent was stripped in vacuo leaving the free base of Ethyl α-[2-(2-pyridyl)ethylamino]phenylacetate Dihydrochloride Hydrate (99 g.) in quantitative yield. The dihydrochloride was prepared by dissolving the free base in methanol and treating the solution with methanolic hydrogen chloride. The alcoholic solution was concentrated and the remaining oil was crystallized from isopropanol. The analytical sample m.p. 173°–175° was recrystallized three times from isopropanol.

Anal. Calcd. for C$_{17}$H$_{20}$N$_2$O$_2$·2HCl·H$_2$O: C, 54.40; H, 6.45; N, 7.47; Cl, 18.89. Found: C, 54.63; H, 6.03; N, 7.54; Cl, 18.97.

EXAMPLE II

α[2-(2-Pyridyl)ethylamino]phenylacetic acid Dihydrochloride Hemihydrate

The free base of Example I (59 g., 0.21 mole) was treated with sodium hydroxide (12.4 g., 0.31 mole) in 100 ml of water. The material was heated at 65°–70° for 10 minutes and then stirred at room temperature for 1 hour. The resulting mixture was extracted with ethyl ether (2 × 200 ml) and the aqueous layer was treated with 6N hydrogen chloride and filtered. The aqueous solution was cooled to yield 40 g. (57%) of the desired product. The analytical sample, m.p. 196°–198°, was recrystallized twice from ethanol.

Anal. Calcd. for C$_{15}$H$_{16}$N$_2$O$_2$·2HCl·½H$_2$O: C, 53.26; H, 5.66; N, 8.28; CL, 20.96. Found: C, 53.27; H, 5.50; N, 8.13; Cl, 21.15.

What is claimed is:
1. A compound of the formula:

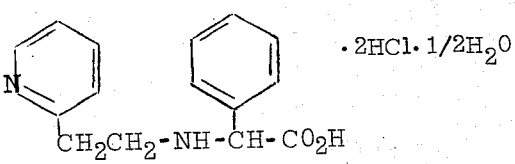 · 2HCl · 1/2H$_2$O

* * * * *